United States Patent
Snyder et al.

(10) Patent No.: US 9,672,472 B2
(45) Date of Patent: Jun. 6, 2017

(54) SYSTEM AND METHOD FOR MANAGING BEHAVIOR CHANGE APPLICATIONS FOR MOBILE USERS

(71) Applicant: Mobiquity Incorporated, Wellesley, MA (US)

(72) Inventors: Scott Andrew Snyder, Berwyn, PA (US); Gregory Paul Rozal, Winsted, CT (US); Andrew Nanopoulos, Wakefield, MA (US); Stephen Tyler Rollin, Marlborough, MA (US)

(73) Assignee: Mobiquity Incorporated, Waltham, MA (US)

( * ) Notice: Subject to any disclaimer, the term of this patent is extended or adjusted under 35 U.S.C. 154(b) by 183 days.

(21) Appl. No.: 13/913,117

(22) Filed: Jun. 7, 2013

(65) Prior Publication Data
US 2014/0365408 A1    Dec. 11, 2014

(51) Int. Cl.
*G06N 5/02*    (2006.01)
*G06N 99/00*    (2010.01)

(52) U.S. Cl.
CPC .................................. *G06N 99/005* (2013.01)

(58) Field of Classification Search
None
See application file for complete search history.

(56) References Cited

U.S. PATENT DOCUMENTS

| | | |
|---|---|---|
| 4,717,343 A | 1/1988 | Densky |
| 5,207,580 A | 5/1993 | Stretcher |
| 8,150,707 B2 | 4/2012 | Hayet et al. |
| 8,275,419 B2 | 9/2012 | Sundaresan et al. |
| 8,299,930 B2 | 10/2012 | Schmid-Schonbein et al. |
| 8,398,546 B2 | 3/2013 | Pacione et al. |
| 2013/0311917 A1 | 11/2003 | Bar-or et al. |
| 2006/0019225 A1 | 1/2006 | Orman |
| 2006/0247956 A1 | 11/2006 | Rosen et al. |

(Continued)

FOREIGN PATENT DOCUMENTS

WO    WO2013168068 A1    11/2013

OTHER PUBLICATIONS

International Search Report for international application PCT/US2014/041182.

(Continued)

*Primary Examiner* — Kakali Chaki
*Assistant Examiner* — Michael Zidanic (57) ABSTRACT

An example system and method for managing behavior change applications for mobile users is disclosed. In an embodiment of the system and method, data on a plurality of users in a behavioral change program is received from a plurality of devices operating in a communications network. The data is used to determine plurality of user segments. Each user of the plurality of users is classified into a one of the plurality of user segments. Then a plurality of behavioral models is determined, where each of the plurality of behavioral models comprises a statistical model of relations between behaviors of users within a corresponding one of the plurality of user segments. An intervention model is then determined for a user, where the intervention model is based on a behavior model of the user segment to which the user belongs. Interventions are then sent to a device of the user according to the intervention model.

16 Claims, 4 Drawing Sheets

(56) References Cited

U.S. PATENT DOCUMENTS

| | | | |
|---|---|---|---|
| 2008/0126277 A1 | 5/2008 | Williams et al. | |
| 2012/0227064 A1* | 9/2012 | Neill | H04N 21/4532 725/14 |
| 2012/0264446 A1 | 10/2012 | Xie et al. | |
| 2012/0303573 A1 | 11/2012 | Pan et al. | |
| 2012/0308970 A1 | 12/2012 | Gillespie et al. | |
| 2013/0004923 A1 | 1/2013 | Utter | |
| 2013/0074129 A1 | 3/2013 | Reisman | |
| 2013/0116939 A1 | 5/2013 | Dai et al. | |
| 2013/0124218 A1 | 5/2013 | Maslowski et al. | |
| 2014/0004492 A1 | 1/2014 | O'Reilly et al. | |
| 2014/0201120 A1* | 7/2014 | Lydon | G06F 21/316 706/46 |

OTHER PUBLICATIONS

James O. Prochaska, Wayne F. Velicer, "The Transtheoretical Model of Health Behavior Change", The American Journal of Health Promotion, 1997, pp. 38-48, vol. 12 issue 1.

James O. Prochaska, "Stages of Change and Decisional Balance for 12 Problem Behaviors", Health Psychology, 1994, pp. 39-46, vol. 13, No. 1.

Anath Sankar, "Bayesian Model Combination (BAYCOM) for Improved Recognition", IEEE International conference on Acoustics, Speech and Signal Processing, proceedings 2005, pp. 845-848.

N. Lathia, V. Pejovic, K. Rachuri, C. Mascolo, M. Musolesi, P. J. Rentfrow, "Smartphones for Large-scale Behavior Change Interventions", Pervasive Computing, IEEE, vol. 12, Issue 3, Jul.-Sep. 2013, pp. 66-73.

Charles Abraham, Susan Michie, "A Taxonomy of Behavior Change Techniques Used in Interventions", Health Psychology, vol. 27, No. 3, 2008, pp. 379-387.

Brianna S. Fjeldose, "Behavior Change Interventions Delivered by Mobile Telephone Short-Message Service", American Journal of Preventative Medicine, 36(2), 2009, pp. 165-173.

Qualcomm Whitepaper "The Future of Mobile Health", published 2011, retrieved on Jul. 29, 2014 at http://www.qualcommlife.com/images/pdf/QualcommLife_Whitepaper.pdf.

Karen Glanz, Barbara K. Rimer, K. Viswanath,"Health Behavior and Health Education", Jossey-Bass 2008, pp. 8, 13-14, 117,143-144, 182-184, 201, 363-387, 390-396, 487-508.

International Preliminary Report on Patentability for international application PCT/US2014/041182, published Jul. 2, 2015.

* cited by examiner

SYSTEM AND METHOD FOR MANAGING BEHAVIOR CHANGE APPLICATIONS FOR MOBILE USERS

TECHNICAL FIELD

This disclosure relates in general to behavior change systems and, more particularly, to a system and a method for managing behavior change applications for mobile users.

BACKGROUND

Behavioral change methods are used to assist persons in modifying behaviors when the behaviors must be changed in order to reach a particular goal. Generally, the purpose of a behavioral change method is to provide interventions with a person over a period of time to form long term consistent behaviors. For example, persons having a chronic disease may need to modify their current behaviors until they reach the goal of permanently adhering to or complying with a medication and treatment regime. Examples of persons needing to modify their current behaviors may include persons on a weight loss program, type 2 diabetics, alcoholics, or drug addicts. Generally, behavioral change methods can be applied to any aspect of human behavior where it is desired to modify the behavior. Because of the need in modern society for behavioral change, it be would provide an advantage to have an improved system and method for managing behavior change that allowed current state of the art technology to be applied to behavior change methods.

DETAILED DESCRIPTION OF EXAMPLE EMBODIMENTS

Overview

A system and method for managing behavior change applications for mobile users is disclosed in accordance with example embodiments. The example embodiments disclose system components and associated programming platforms that provide application programming interfaces for supporting a system and method of managing behavior change applications. The application programming interfaces support the features and functionalities, access to databases, and the data and information flow for web or mobile based device applications that receive information associated with users of the applications or deliver interventions to users of the applications. The interventions may be in the form of notifications (e.g., visual, audible or haptic) or other data information delivery to the user.

In one example embodiment of the system and method, the system and method is implemented as a behavioral change system comprising applications that may be implemented on mobile devices and software applications that may be implemented on one or more server computers. The mobile devices may be smart phones or tablets, or other types of mobile devices, such as wearable devices that include sensors for detecting activity or sensing data on physical or environmental conditions. The embodiment may include web based applications accessible using desktop or laptop computers. The embodiment of the behavioral change system also includes functional modules implemented on one or more server computers that control data collection and integration, data analysis, and interventions with the users. In the embodiment, the mobile devices are utilized to receive, through user input or sensors, data and information associated with the users of the devices and transfer the data to the server computers. A data fusion module collects and integrates the data and the data is input to a behavior analytics module. The behavior analytics module processes the user level data stored in the various databases of the data fusion module and constructs user segments and describes behavior patterns associated with the user segments into behavior models. Each of the users is classified into a one of the plurality of user segments. The behavioral models comprise a statistical model of the user behavior patterns within a corresponding one of the user segments. The behavior models may then be utilized in the design of intervention models that define sets and sequencings of interventions. The intervention models form rules that may be used as inputs to a mobile/website intervention module that determines a user's current state, or determines a highest probability state of the user, and assigns an intervention model to the user based on the user's determined state. The intervention model is based on a behavior model of the user segment to which the user has been determined probabilistically to belong. The interventions may then be sent to, or triggered at, the mobile device or computer web browser of the user in the form of notifications (e.g., visual, audible or haptic) or other data information delivery to the user. In the example embodiment, the intervention module may also include an analytical reporting interface that measures a user's response to interventions in terms of behavior change metrics for feedback to the behavior analytics module.

Example Embodiments

Figure 1A:
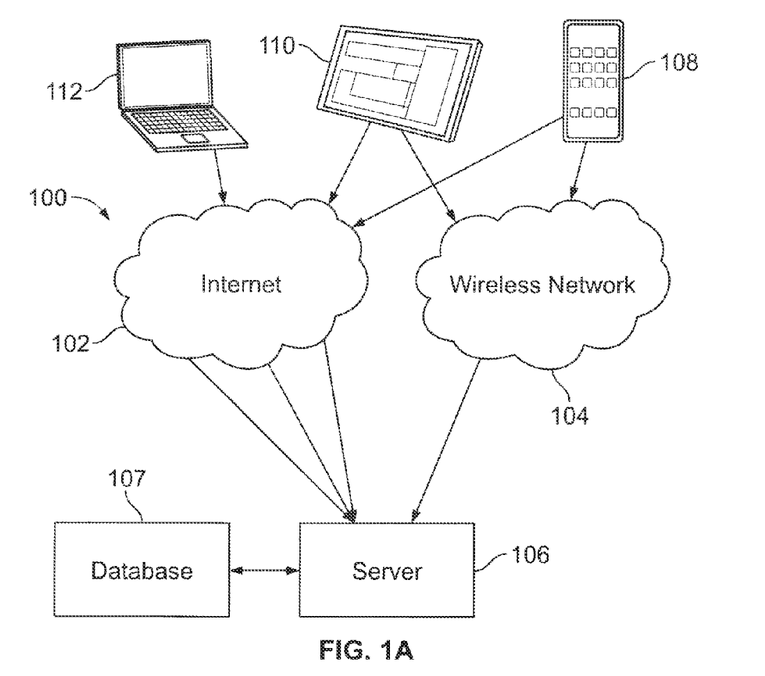
FIG. 1A is a simplified block diagram that illustrates an example communication system into which an embodiment of the disclosure may be implemented.

Referring now to FIG. 1A, therein is a simplified block diagram that illustrates an example communications system into which an embodiment of the disclosure may be implemented. The communication system, shown generally by reference numeral 100, comprises devices which may be implemented, for example, by smart phone 108, tablet 110 and laptop 112. Applications are implemented on smart phone 108, tablet 110 and laptop 112 that provide the necessary data collection and interventions for functioning of the embodiment. Any other type of device, such as a desktop personal computer, that may be operable to communicate the appropriate data may also be used in the system and method of the embodiment. Communication system 100 also includes internet network 102 and wireless network 104 over which the mobile devices 108, 110 and 112 communicate with server 106. Internet network 102 and wireless network 104 may each comprise any appropriate radio communication and/or infrastructure equipment that implements communications between mobile devices 108, 110 and 112 and server 106 using appropriate internet or wireless network communication protocols. The communications interfaces between smart phone 108, tablet 110 and laptop 112 and internet network 102 and wireless network 104, and, the interfaces between internet network 102, wireless network 104 and server 106, may also be implemented using any appropriate radio communication and/or infrastructure equipment. Although one server 106 and database 107 are represented in FIG. 1A, the functions represented by server 106 and database 107 may actually be implemented in one or more servers and one or more databases, and those functions or portions of those functions may co-located or separated geographically in location. Server 106 may comprise software, hardware and software applications as necessary to implement the features and functions of the embodiment of the system and method.

Figure 1B:
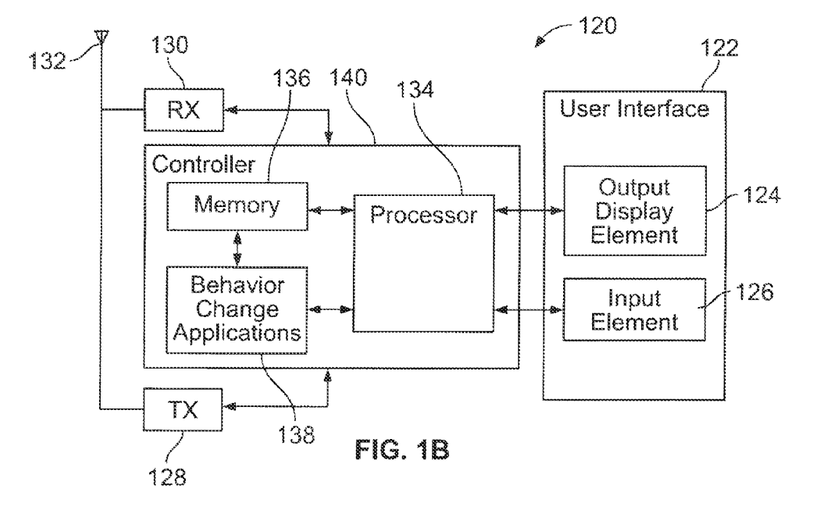
FIG. 1B is a simplified block diagram that illustrates an example implementation of a mobile device in accordance with an embodiment of the disclosure.

Referring now to FIG. 1B, therein is a simplified block diagram that illustrates an example implementation of an example device in accordance with an embodiment of the disclosure. Mobile device 120 comprises receiver RX 130, transmitter TX 128, controller 140 and User Interface 122. RX 130 and TX 128 receive and transmit data and communications to and from server 106 over network 100. Controller 140 comprises processor 134, memory 136 and behavior change applications 138, which, for example, may be stored as program instructions in a memory of Controller 140. In the example embodiment, behavioral change applications 138 include behavioral change applications that cause mobile device 120 to function to communicate with server 106, collect and receive data, and, receive and present data at User Interface 122, as necessary to implement the functions of the embodiment. User Interface comprises output element 124 for outputting data, notifications and interventions to a user, and input element 126 for receiving input from the user. Output element 124 may comprise any interface for providing notifications and interventions to the user in a sensory manner, such as visual, audio, vibrating, or any other sensory means, including, for example, a visual display, an alarm, an audio player, or a vibrator. Input element 126 may comprise any element for inputting data to mobile device 120 such as, for example, a keyboard, touch screen, audio input, motion detector, location detector, biometric sensor, or other type of sensor.

Figure 2:
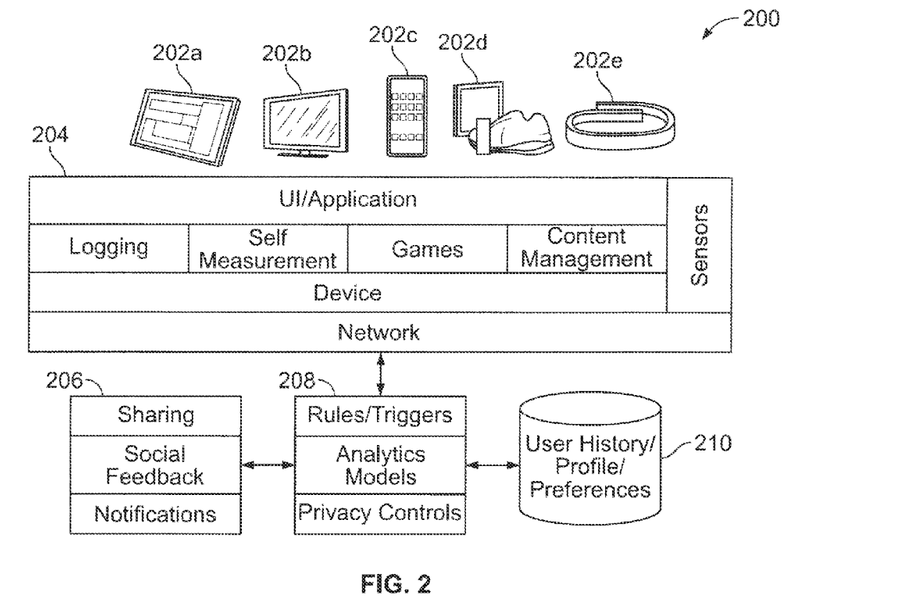
FIG. 2 is a simplified block diagram illustrating functional blocks of a example system into which an embodiment of the disclosure may be implemented.

Referring now to FIG. 2, therein is a simplified block diagram illustrating functional layers of an example embodiment of a system 200 in accordance with the disclosure. FIG. 2 shows hardware layer 204 including user interface (UI)/ Application layer that communicates with devices, shown in FIG. 2, as tablet 202a, desktop computer 202b, smart phone 202c, wireless exercise equipment 202d and wireless bracelet 202e. Each of the devices interfaces with the system 200 through the user interface and applications (UI/Applications) that, in conjunction with sensors, provide the functions of logging, self measurement, games and content management to generate data and interventions for users of the devices. The devices communicate through the network with functional block 208. Functional block 208 receives data from the devices over the network, applies analytics and creates models and rules and triggers drawing on user history and profile preference form block 210. Functional block 208 also may receive process and integrate other types of data such as, for example, data and inputs from sharing, social feedback, and notifications on social networks and notifications.

Figure 3:
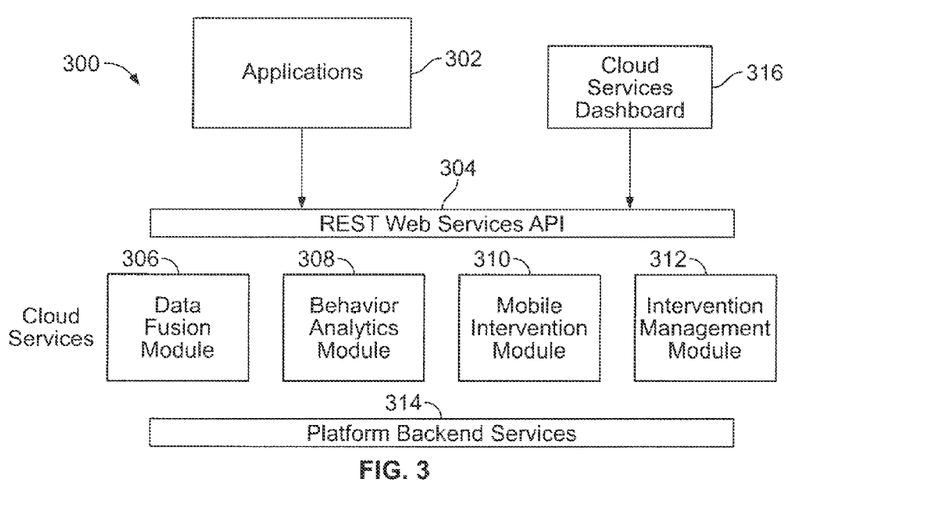
FIG. 3 is a simplified block diagram illustrating further functional blocks of an example embodiment of the disclosure.

The embodiment of FIGS. 1 and 2 allows user data input from a plurality of devices and digital entry or touch points, for example, native applications in mobile phones, computer web browsers, biometric sensors and other devices such as digital televisions, etc. It allows the collection of contextual (e.g., location, etc.) and environmental data (e.g., noise, temperatures, photos, videos, etc.) related to the user from the output of sensors (e.g., microphones, cameras, accelerometers, gyros, etc.) in a mobile device or computer. Other types of data (e.g., links, activity frequency, texts, messages and images, etc.) from Social Networks may also be included in the collecting and processing. Data from a wide variety of sources, frequency, and formats may be integrated to estimate the user's behavior and context Referring now to FIG. 3, therein is s a simplified block diagram illustrating functional blocks of a system 300 implemented in accordance with an example embodiment of the disclosure. FIG. 3 shows the functional software module blocks of mobile applications 302, REST Web Services API 304, and platform backend services 314 that comprise Data Fusion Module 306, Behavior analytics Module 308, Mobile Intervention Module 310, and Intervention Management Module 312. These functional modules may be implemented into a system, for example system 100 of FIG. 1A to create a system and method according to an embodiment of the disclosure. The applications of module 302 may be implemented on the mobile devices 108, 110, 112 (FIG. 1A) and 202a-202e (FIG. 2). Applications 302 may receive and collect data from the user and the environment and deliver the interventions that promote desired behavior change. The Application 302 may be downloaded to the mobile device or be preinstalled. Applications 302 may include applications that interact directly with a user through an interface, such as User interface 122 of mobile device 120 of FIG. 1B, to receive inputs and provide outputs to the user. Applications 302 may also include components such as, for example, a Web-based application that can be accessed using a desktop computer or laptop with relatively more screen space, for example than a smart phone, that will allow the display of multiple charts and information simultaneously. Applications 302 also may be implemented in wearable devices with sensors that can detect physical activity, and environmental data, such as wireless bracelet 202e of FIG. 2. The wearable devices may be programmable to vibrate as needed to provide another means for reminding or alerting the user. Applications 302 may collect, receive and, deliver data in any form. For example Applications 302 may provide digital entry forms, e.g., survey forms, for the end-user to fill-in, or user interaction features such as page/screen views, with clicks or taps to enter responses or information. Applications 302 may also collect data such as location data from a GPS device or IP Addresses from web browsers. Collected data may also include data collected from sensors, for example, microphones, accelerometers, thermometers, etc. These sensors may provide the data on sound, positional location, movement, physical condition of a mobile user, or the environment of a mobile device or of a user of a mobile device. Applications 302 also may utilize the hardware aspects of mobile devices 108, 110, 112, and 202a-202e to deliver interventions to the user in order to implement the embodiments of the disclosure.

The Platform Backend Services 314 that comprise Data Fusion Module 306, Behavior analytics Module 308, Mobile Intervention Module 310, and Intervention Management Module 312 may be implemented in one or more servers such as server 106, and one or more databases such as database 107 of system 100 of FIG. 1A. Communication between the Applications 302 and Platform Backend Services may be implemented using REST Web Services API 304 as the interface. The various functions necessary for the Platform Backend Services 314 may be implemented by software or hardware or by a combination of software and hardware. Although the functions represented by Data Fusion Module 306, Behavior analytics Module 308, Mobile Intervention Module 310, Intervention Management Module 312 and Cloud Services Dashboard 316 are shown as single modules, those functions may actually be implemented in one or more servers and one or more databases, and those functions or portions of those functions may co-located or separated geographically in location.

Figure 4:
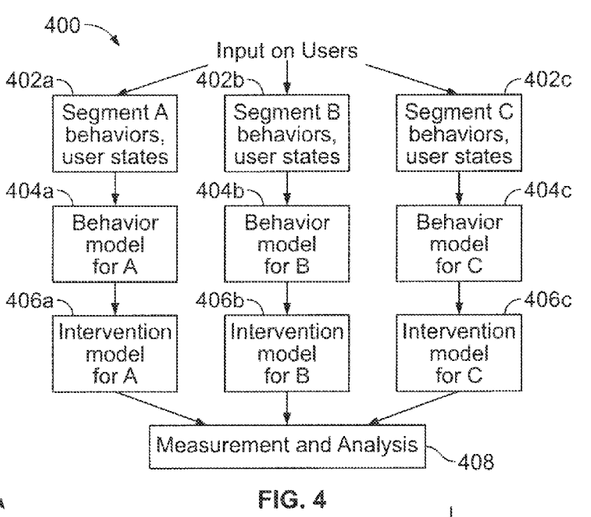
FIG. 4 is a simplified flow diagram illustrating example operations of a process in accordance with an embodiment of the disclosure.

Referring now to FIG. 4, therein a simplified flow diagram illustrating example system level process operations 400 in accordance with an embodiment of the disclosure. Generally, input on a plurality of users 401 is received and a plurality of user segments A-Care determined, at 402a-402c, based on analysis of the received data. A behavior model is then determined for each user segment A-C, at 404a-404c, and, then an intervention model for each user segment A-C, is determined at 406a-406c. Measurement and analysis is then performed on the use of the intervention models to determine effective of results. That information may be feed back into the system for use in development of the parameters used in the determinations of the user segments, behavior models, and intervention models.

Figure 5A:
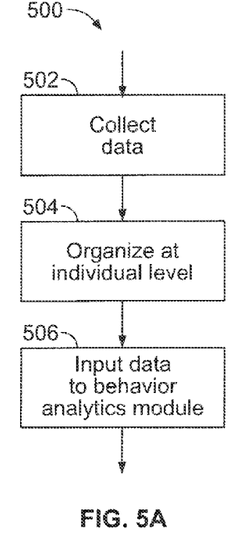
FIGS. 5A and 5B are a simplified flow diagrams illustrating an example process in accordance with another embodiment of the disclosure; and, FIG. 6 is a simplified block diagram illustrating an example of a behavioral model with an intervention model in accordance with an embodiment of the disclosure.

Referring to FIG. 5A, therein is shown a simplified flow diagram 500 illustrating example processes performed by Data Fusion Module 306 (FIG. 3) in accordance with a an embodiment of the disclosure. At operation 502, Data Fusion Module 306 collects the data on mobile users received from Applications 302. The Data Fusion Module 306 is configured to accommodate data from any of the data sources, at any frequency of collection or input, and in any of the formats that may be used by Applications 302 to collect and send data. Data Fusion Module 306 also may receive data from social networks, for example, network graphs, frequency of activity, texts, messages and images, etc. This data may be included in the databases in the Data Fusion Module 306 and utilized in the analytics and models of the embodiments of the disclosure. At operation 504, Data Fusion Module 306 organizes data at the individual user-level and, at 506, inputs this data to Behavior Analytics Module 308. Behavior Analytics Module 308 stores, manages, accesses and extracts data of, and for an individual user to create a complete view of the user including the user's physical environment and social situation Data Fusion Module 306 may use a combination of relational databases and NoSQL data stores (e.g., document and graph databases) to store user information. The user information may include, for example, health profiles and reminder preferences, transactional data with the applications (e.g., mobile, Web and sensor logs, user input/generated content, etc.) and third-party source data, such as hourly weather (e.g., precipitation and temperature), macroeconomic indicators (e.g., DJIA) and major news events. The user data may also include information on relationships between users (e.g., caregivers, friends and relatives.)

The system may collect the data linked to an individual via a unique identifier (User ID). The User ID may be an anonymous token, i.e., not personally identifiable information and may be used by Data Fusion Module 306 process and categorize the data appropriately. Data Fusion Module 306 may be configured to allows querying and extraction of data by User ID and the data at the user-level may be configured to be configured to build statistical behavior models. Extracted data may be in the form of data cubes, i.e., a matrix with rows containing data about a User ID and columns containing values for attributes of users collected over time periods. User attributes may include a user profile including, for example, age, gender, health status & biometrics, weight, blood glucose level, glycosylated hemoglobin (A1c), blood pressure, etc., medication intake, caloric intake, physical activity and user emotional states (e.g., happy, sad, anxious, lonely) measured and/or summarized over time periods (minutes, hours, daily, weekly, monthly, etc.)

Figure 5B:
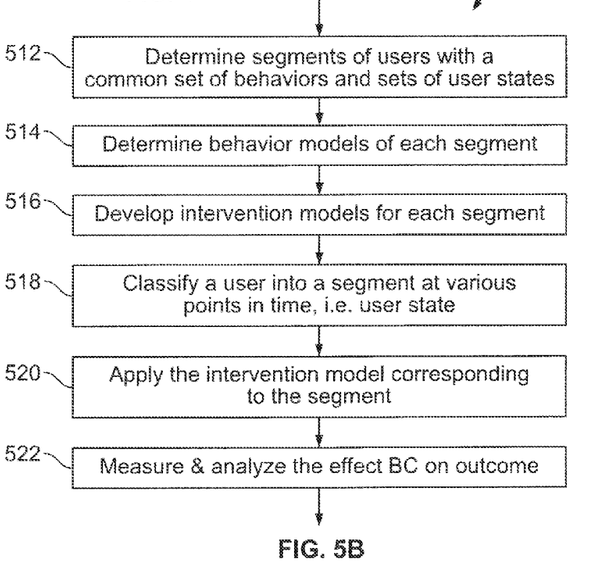

Referring now to FIG. 5B, therein is a simplified flow diagram illustrating example processes performed by Behavior Analytics Module 308 and Mobile Intervention Module 310 in accordance with the embodiment of the disclosure. At operation 512, of FIG. 5B, Behavior Analytics Module 308 utilizes the data available in the system to determine user segments based on a common set of behaviors and sets of user states. The data used may include data on a plurality of users of the system stored in data fusion module 306. At operation 514, Behavior Analytics Module 308 then determines behavior models for each of the user segments. The behavior modules may then be used to develop intervention models at operation 516. The operations of 512 through 516 may be continuously performed, as necessary, as data is collected and received from a plurality of users of the system over a period of time. The User segments and behavior models may be added or revised as collected and received data is process. The data used in operations 512 through 516 also may include data received from Intervention Management Module 312 on measurements of responses and results of the application of interventions on users. This data from Intervention Management Module 312 may be used to refine the behavior and intervention models for each user segment. Cloud Services Dashboard 316 provides functionality by which a system administrator can control which features, functionalities and interventions are turned on or off. This may be used for clinical research, for example, for studying and measuring the effects of interventions in various combinations. Cloud Services Dashboard 316 also provides for control of measurement and analysis of the user responses, i.e., the outward manifestations of Behavior Change, to the interventions through a reporting and analytics interface.

Referring again to FIG. 5B, application of the process to the users of the system begins at 518, where a user is classified into a segment. This may happen for various users at various points in time depending on the users and on the system configuration. At 520 the mobile Intervention Module 310 applies the intervention model corresponding to how the user has been classified and at 522 Intervention Management Module 312 is used to measure and analyze the effect and outcome of the intervention on behavior change. While the process operations of FIG. 5B are shown in a particular sequence, the operations may be performed in any appropriate sequence and operations may be added or omitted as various iterations of the process is performed.

The Behavior Analytics Module 308 receives the data as user-level data stored in various databases in the Data Fusion module 306, and utilizes the data to determine user segments. User segments are groups of users that exhibit characteristics of having, to a predefined degree, a common set of behaviors and user characteristics. The segment profile describes a user segment and may include a summary description, which may be statistical, of the behavior characteristics of the users in the segment. For example, a user segment may be defined for people who have expressed a desire to lose weight, average exercise, i.e., any physical activity for at least 30 minutes, less than 3 times a week, and a preference for mobile apps to remind them to exercise. Behavior Analytics Module 308 may use clustering methods to discover user segments. Behavior Analytics Module 308 can discover user segments from which behavior models can be developed including description of user states and behavior patterns, for example, users that exercise less than 3 times a week, drink alcohol excessively to reduce stress or "unwind," or engage in "nervous" overeating.

Behavior Analytics Module 308 may also include behavior models. Behavior models are sets of user states (e.g., medication compliant or not, low physical activity, problem drinker, active substance abuser, etc.) and their behavior patterns (i.e., states and the possible sequence of transitions/actions from state to another including the transition probabilities estimated from the historical data.) For example, overweight users that tend not to engage in physical activity and tend to "overeat," or problem drinkers that have a 90% probability of drinking alcohol after work to "unwind" or to relieve work-related stress. Stochastic equations or probabilistic graphical network models, e.g., Structural Equations, Hidden Markov Models or Bayesian Networks, can be used to represent behavioral models. User behavior models are used to design intervention models. Given a behavior model, a sequence of interventions can be activated to prevent the continuation, or modification of the current behavior. For example, users can be given reminders at the start of certain days to exercise, or problem drinkers that drink alcohol from stress can be given scheduled reminders and alerts at certain times in a day or in a week through their mobile device or computer. These intervention models are rules that can be inputs to the Mobile/Website Intervention Module 312.

In the example embodiment Behavior Analytics Module 308 may operate on data classes that have been collected from users of the system by Data Fusion Module 306, that include outcome or success metrics, behavior or activity metrics, user states, environmental factors, and user identifiers. Outcome or success metrics are measurable results collected over time that are the object of the behavior change. For example, in alcohol moderation, an outcome may be the number of continuous days of alcohol abstinence. If the object of behavior change is medication adherence, an outcome may be the percentage of days when medication is taken, or in the case of diabetics, outcome may be blood, glucose and/or A1c levels. In a weight loss program, an outcome metric may the weight and body mass index of individuals in the weight loss program. The data classes of behavior or activity metrics are the measurable aspects of the behaviors that the user intends to change, measured over time. For example, in alcohol reduction, the days when no alcohol is consumed. In medication adherence a behavior activity metric may be the logging of a pill ingestion event. In a weight loss or blood sugar management program a behavior activity metric may be the date, time, length and intensity of an aerobic exercise or calories in meals for an individual in the program. The data classes of user states are states or conditions internal to the user that affect the user's ability or belief to change behavior, for example, age, gender, diseases, medical or physical conditions, emotional states, motivations, commitment to change, emotional resiliency, and preferred mode or modes of intervention. These states are assumed to change to over time. The data classes of environmental factors are external conditions that affect the user's ability or belief to change behavior, for example, weather, stressful or pleasant events, size and strength of social networks, and economic conditions. Environmental factors may change over time. The data classes of user identifiers may be, for example, keys, possibly anonymous and that may be used to match user's data from one data class to another.

Behavior Analytics Module 308 may use Cluster Analysis or other means, to create user segments from one or more combinations of user attributes in the data classes. For example, the user attributes of age, gender, medical/physical conditions (e.g., type 2 diabetes, hypertension, dyslipidemia), biometrics (e.g., BMI, blood pressure, A1c, cholesterol, triglycerides, blood glucose levels), medications and their intake (medication adherence), daily caloric intake, weekly average amount of physical activity, stated level of commitment to change, and preferred modes of intervention may be used to find user segments. Initially, this Module may find a segment of people who have expressed a desire to lose weight, but exercise an average of less than 3 times a week, and prefer to use mobile apps as intervention tools. This segment could be further sub-divided into age and into gender with or without medical/physical conditions. For example, one sub-segment could be 45-54 year old diabetic males with BMI between 25-30, hypertensive and have higher than normal total cholesterol (above 160 mg/dL). Another sub-segment could be 35-44 year old females with BMI over 30.

Figure 6:
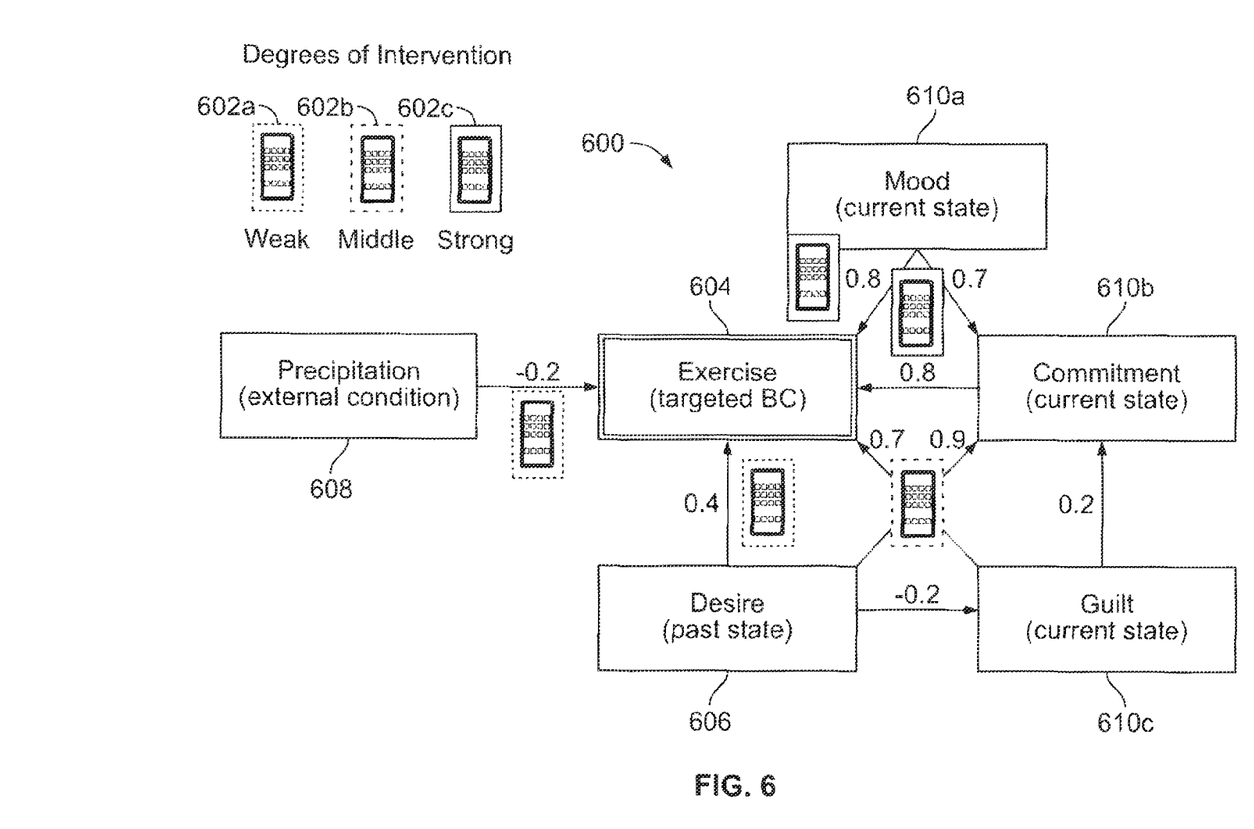

For each user sub-segment, a behavior model may be developed. The behavior model may be a description of the relationships between the user's measurable behaviors and the physical, emotional and environmental states and conditions that affect these behaviors. These relationships can be represented, for example, by a system of equations, or graphically as in FIG. 6. Referring now to FIG. 6, therein is a simplified block diagram illustrating an example intervention model in accordance with an embodiment of the disclosure. FIG. 6 shows the correlation coefficients of states and intervention levels. States are shown as the current states of mood 610a, commitment 610b, and guilt 610c, the past state of desire 606, and the targeted state of exercise 604. External condition precipitation 608 is also shown in the model. The arrowed lines between the states show correlation coefficients that may have degrees of intervention as weak 602a, middle 602b and strong 602c as indicated by dotted, dashed and solid lines, respectively. The behavior model may also include a possible set of interventions that could be applied to affect these behaviors in the model. While some of the user states and conditions of the embodiment may not be directly observable, the Behavior Analytics Module 308 may estimate the most likely state or condition a user is in at the present time based on historical data recorded about the user. The behavior models may be derived by applying a combination of statistical methods to the historical user-level behavior data. To illustrate, Principal Components Analysis may be used to determine the sets of behavioral variables or concepts that can explain the most variation in user behaviors. Having reduced the variables to a few that significantly explain behavior patterns, Factor Analysis, or the more general Structural Equation Modeling, may be used to estimate the direction (positive or negative sign) and the strength, if any, (coefficients) of the correlations of the relationships between these variables. Another approach is to use Hidden Markov Models, or the more general Bayesian Networks, to describe the relationships between these behavioral variables.

In an example implementation, Behavior Analytics Module 308 may use User ID-level data that can be extracted from the Data Fusion Module to apply Cluster Analysis utilizing, for example, hierarchical, k-Means, distribution model, or density-based methods, to find clusters or segments of "like" users based on User IDs from a set of predetermined attributes. Cluster Analysis may be applied to the following variables: age, gender, weight, blood glucose, A1c, % medication adherence rate, average daily caloric intake, weekly physical activity, and daily mood patterns for a week. An example of a possible user segment that may come up with Cluster Analysis is a segment of users with A1c between 8-10%, daily caloric intake >3500, and low physical activity with a 50-75% medication adherence. Because Cluster Analysis is a non-linear statistical method it is possible that while some variables that are discriminating factors in some segments, they may not be in other segments.

In the embodiment, communication and motivational preferences of a user may be determined from direct input or historical data and considered in determining the appropriate intervention. For, example, some users know they respond better to text reminders versus leaderboards and the users may indicate or "input" these preferences in the application settings. Historical behavior of the user may also be considered in determining the appropriate intervention. For example, users that have consistently followed their prescribed regimen of medication, physical activity and caloric intake, regularly with only a few slips may require a different intervention program versus a user that rarely follows their prescribed regimen. Additionally, dynamic changes to the types of interventions that may be applied to a specific user may be made based on observed patterns of behavior and context.

In the example implementation, for each user segment, a statistical model represented by a system of equations is built that relates behaviors, such as medication ingestion, physical activity and caloric intake, self-efficacy, commitment to change, emotional states, time and location, social context and environmental factors like weather and macroeconomics. Conditions that can trigger or expose opportunities for behavior change are identified for use in determining features of the models. For example a behavior model for a user segment that exercise (i.e., any physical activity lasting at least 30 minutes) less than 3 times a week may be represented as a system of equations:

$$\text{Exercise} \leftarrow 0.8 \text{ Mood} + 0.8 \text{ Commitment} + 0.7 \text{ Guilt} + 0.4 \text{ Desire} - 0.2 \text{ Precipitation} + c_1 + \epsilon_1 \quad \text{Equation 1:}$$

$$\text{Commitment} \leftarrow 0.7 \text{ Mood} + 0.2 \text{ Guilt} + 0.9 \text{ Desire} + c_2 + \epsilon_2 \quad \text{Equation 2:}$$

$$\text{Guilt} \leftarrow -0.2 \text{ Desire} + c_3 + \epsilon_3 \quad \text{Equation 3:}$$

where Exercise, Mood, Commitment, Guilt, Desire, Precipitation are indices, i.e., normalized values of the original measurements, the c's are numerical constants, and the $\epsilon$'s are error (random) variables.

A combination of statistical methods including Principal Components Analysis, Structural Equation Modeling, Hidden Markov Models, and Bayesian Networks may be used to derive the system of equations that specify a Behavior Model.

The Behavior Analytics Module 308 may store all user segments and their profiles, as well as the behavior model and intervention model associated with each segment. The segment profiles describe each segment in terms of the parameters and value sets of the segment variables. For example a user segment could be users with A1c between 8-10%, daily caloric intake >3500, and low physical activity with a 50-75% medication adherence. Each user segment will have a behavior model and an intervention model assigned to it. Symbolically, let User Segment A={all users with values x∈A} where x is a vector of measurements about a user, and A describes a set of values for each measurement, with Behavior Model A={derived set of stochastic equations}, and Intervention Model A={set of rules: if [conditions] are true, then do [intervention]}.

Interventions in the behavioral change system are physical stimuli that can be delivered via mobile, Web app, or wearable devices, which may be the devices and interfaces that also, collect data from the user and their environment. The interventions in the example implementation may be as described earlier. These interventions can be active. An active intervention may be pushed to user or require an action or response from the user to be completed. The interventions may also be passive, for example, available information that requires the user to open a screen like the e-pillbox or dashboard. Active interventions, for example, alerts and reminders, are pushed to the user when conditions exist (whether internal or external to the user) in which an intervention would produce a desired, corrective change in behavior. The Intervention modeling performed by Behavior Analytics Module 308 is a process of specifying conditions, for example, user states, biometrics, time of day, location, environment, social context, etc., that will activate interventions or intervention serving rules. These rules or algorithms are used in the Intervention Module. For example, a serving rules may be actions such as an action to send a morning alert to user at 7 am if the users smart phone has not been turned on at that time, to play a dance music audio clip at 12 noon, if no physical activity has been logged at that time by that user, or to send an image of a beloved child at 7 pm if the caloric intake of a user is already above 3000 by 2 pm.

The interventions may include a visual tracker of medication adherence, for example, an "e-pill box", reminders, such as, for example, a SMS push notification to the user of a next dose, audible and text alerts if the user has passed the grace period and is about to miss a dose. Fail to adhere interventions can include user-generated content instead of the system-provided text messages and sounds. For example, pictures or videos of loved ones, and inspirational text and sounds, can be uploaded to the behavioral change system and used for reminders and alerts. Other interventions may include dashboards displayed to a user showing adherence rate metrics (e.g., % of adherent days over the number of days, etc.) over predetermined time periods, for example, 3, 7, 14, or 30 days. The dashboard may also include a health outcome trajectory based on the current medication adherence rate that is compared with the trajectory for an ideal 100% adherence. The interventions may also include mobile notifications on positive reinforcement. For example, points may be awarded and notified to a user when certain milestones are reached or badges may be earned and notified to a user for other activities that help the effectiveness of the treatment are completed or performed. The system may monitor milestones and activities such as, for example, every achieved day of adherence, achievement of 100% adherence over a 2-week period, the reading literature about the disease and treatment options, achievement of 30-days of a predetermined level of physical activity, or maintenance of a specific weight. The interventions may also included display of a leader board that shows a user's adherence rate as it compares against others in a certain age-gender group. Additionally, selected information may be shared or automatically sent to designated caregivers or health care providers with confirmation that they have received the selected information.

In the embodiment, Mobile Intervention Module 310 may determine the user's current state or the state with the highest likelihood to which the user belongs, and assign and apply an intervention model. The intervention model defines the set and sequencing of interventions. For example, to reduce or eliminate alcohol consumption or overeating triggered by an emotional response to stress interventions delivered through the delivery of user uploaded images of loved ones with along with a self-written promise or inspirational message may be part of the intervention model.

The intervention model is structured to include a list of user states and their operational descriptions. At any point in time, a user has a likelihood or distance to a specific user state, based on the current data about the user. The intervention model may define the state with the highest likelihood as the user's current state. In the embodiment, each user state is mapped to an intervention model. The set and sequencing of interventions of the intervention model includes when interventions can be triggered or sent to the user's device, e.g., mobile or computer web browser. Additionally, the user's preferences for different intervention types (text, leader boards, etc.), which the user can provide via direct input, or which can be determined from historical data, may be considered in determining the appropriate intervention. The Mobile Intervention Module 310 may include and manage the interventions using classes (e.g., reminders and alerts, user-generated content, educational/ information, graphical feedback, and Social Feedback.

The Intervention Management Module 312 determines the set of interventions that are active to the user's mobile device or computer web browser. The default setting for a user is that all interventions are inactive. Intervention Management Module 312 can be used to activate experimental interventions in different combinations to measure the main interaction effects on behavior change. This may be used to research and develop optimal interventions for various user states. Intervention Management Module 312 may be operated by a system administrator who may activate interventions, or sets of interventions for various sets of users. Intervention Management Module 312 may include an analytical reporting interface that measures the user's response to the interventions in terms of the Behavior Change metrics. These behavior change metrics may be for example, health outcomes, days since last alcohol consumption, etc. Intervention Management Module 312 may then be used to determine what interventions produce the best responses and depending on the objective of the Behavior Change application, these interventions can selectively be applied users.

The Intervention Management Module 312 uses serving rules to send interventions or make interventions possible (as in the case of passive interventions like Dashboards) to the mobile, to the Web or to wearable sensors. This module collects data about the user via the applications (mobile, Web or sensor). For example, the module determines the time (e.g., time of day, day of week, calendar date) and location of the user and the user's environment (at a noisy location, warm weather over 90 degrees Fahrenheit, etc.), social context and recent information about the user (e.g., most recently measured biometrics like weight, blood glucose level, A1c, current % medication adherence rate, last time medications were taken, average caloric intake in the last 24 hours, last time calories for meals were entered, average physical activity in the last seven days, most recent physical activity entered, amount of sleep in the last 48 hours, and last mood entered.) Intervention Management Module 312 processes and interprets this data in real-time to identify the behavior segment among all the behavior segments described in the Behavior Analytics Module that has the highest likelihood that the user belongs using a metric D. For example, if the Behavior Analytics has three segments described by the following: User Segment A={(x, y, z): $l_{xA}$<=x<=$u_{xA}$, $l_{yA}$<=y<=$u_{yA}$, $l_{zA}$<=z<=$u_{zA}$}; User Segment B={(x, y, z): $l_{xB}$<=x<=$u_{xB}$, $l_{yB}$<=y<=$U_{yB}$, $l_{zB}$<=z<=$u_{zB}$}; and User Segment C={(x, y, z): $l_{xC}$<=x<=$u_{xC}$, $l_{yC}$<=y<=$u_{yC}$, $l_{zC}$<=z<=$u_{zC}$}, etc. where x, y, z are three measurements about users for all segments in the Behavior Analytics Module. We will assume that it is possible to assign a centroid for User Segment. For example, the Centroid of User Segment A=p(A)=$x_A$, $y_A$, $z_A$) where $x_A$=mean of x, $y_A$=median of y, $z_A$=midrange of z) for all (x,y,z) in A. The statistic used for the component of the centroid can vary depending on the measurement. At any point in time a user will have values (f, g, h) for each of the measurements. Let D(A)=Euclidean Distance of (f,g,h) to μ(A),
Where, $$\mu(A) = \sqrt{(f-x_A)^2 + (g-y_A)^2 + (h-z_A)^2}$$

Assign the user to the Segment S* such D(S*)≤D(S) for all segments S. Although unlikely, if there is a tie, that is, there exists a distinct Segment S'≠S* such that D(S')=D(S*) ≤D(S) for all S, then assign user to either S' or S* randomly.

Another metric D' could use likelihood principles. Given historical data, at time t, user has P($A_t$)=probability of belonging in Segment A at time t, P($B_t$)=probability of belonging in Segment B, P($C_t$), etc. One could think of membership in user segments as user states in a stochastic process. Thus, there are transition probabilities of going from one state to another, e.g., P(A→B), P(A→C), P(B→C), etc. Assuming the process has a Markov property, then it may possible to calculate the P($A_t$), P($B_t$) P($C_t$), etc. at any point in time. There are many available methods to estimate these probabilities. Examples include using Hidden Markov Models or Dynamic Bayesian Networks.

If D'(A)=1−P($A_t$) at time t, etc., then the user could be assigned the segment with highest likelihood or lowest D'. The optimal choice of metric used to assign a user to a segment will depend on the Behavior Change objective and the variables used to profile or describe the user segments. This process of assigning a user to a segment happens whenever an update of user's state occurs, i.e., when the values (f, g, h) change. Once a user is "assigned" to a segment S*, then the Intervention Module activates intervention using the serving rules of the intervention S.

Although the present disclosure has been described in detail with reference to particular embodiments, implementations, arrangements and configurations, these example embodiments, implementations, configurations and arrangements may be changed significantly without departing from the scope of the present disclosure. Moreover, although the example embodiments have been illustrated with reference to particular elements and operations that facilitate the communication process, these elements, and operations may be replaced by any suitable architecture or process that achieves the intended functionality of example embodiments. Numerous other changes, substitutions, variations, alterations, and modifications may be ascertained to one skilled in the art and it is intended that the present disclosure encompass all such changes, substitutions, variations, alterations, and modifications falling within the scope of the appended claims.

What is claimed is:

1. A system for managing behavior change applications receiving data associated with a plurality of users operating a plurality of devices in a communications network and delivering interventions to the plurality of users, the system comprising:
one or more servers computers including application programs which when executed cause the one or more servers computers to control the system to:
receive a first data set from a plurality of applications, each of the plurality of applications implemented on one of the plurality of devices and collecting data associated with one of the plurality of users for the first data set, wherein the first data set includes activity information of the plurality of users and user attributes of the plurality of users;
determine a plurality of user segments for a behavioral change program based on the received first data set, the plurality of user segments each including a subset of the plurality of first users;
determine a second data set, the second data set being a subset of the first data set and associated with a selected user segment of the plurality of user segments;
determine a behavioral model for the selected user segment, the behavioral model comprising a statistical model of relations based on the second data set;
receive a third data set from a selected application of the plurality of applications that is associated with a selected user and a selected device, wherein the third data set includes activity information of the selected user and user attributes of the selected user;
classify the selected user into the selected user segment of the plurality of user segments based on the third data set;
determine an intervention model for the selected user based on the behavior model for the selected user segment, and,
send an intervention to the selected application according to the intervention model, wherein the intervention comprises a notification perceptible at the selected device and the intervention is sent to change behavior indicated by the activity information of the selected user.

2. The system of claim 1, wherein the first data set includes activity information associated with a behavioral change program and the application programs further cause the one or more servers to control the system to:
store the first data set in a data fusion module; and,
update the first data set in the data fusion module as activities of the plurality of users take place over time to generate an updated first data set for the plurality of users.

3. The system of claim 2, wherein the plurality of application programs further cause the one or more servers to control the system to:
receive the updated first data set for the plurality of users and update the behavioral model for the selected user segment as the activities of the plurality of users take place over time.

4. The system of claim 1, wherein the intervention comprises a first intervention and the application programs further cause the one or more servers to control the system to send a second intervention to the selected application according to the intervention model in response to receiving a fourth data set from the selected application.

5. The system of claim 1, wherein the application programs further cause the one or more servers to control the system to determine the intervention model for the selected user based on the behavior model for the selected user segment by:
determining a conditional state of the selected user from the third data set; and,
mapping the conditional state to the intervention model.

6. The system of claim 1, wherein the first data set received from the plurality of applications comprises data received from sensors in at least one of the plurality of devices.

7. The system of claim 1, wherein the first data set received from the plurality of applications comprises environmental data, contextual data, data from social networks and data input at a user interface to at least one of the plurality of devices.

8. One or more non-transitory computer readable storage media including instructions that, when executed by one or more server computers, cause the one or more server computers to:
receive a first data set from a plurality of applications, each of the plurality of applications implemented on one of the plurality of devices and collecting data associated with one of the plurality of users for the first data set, wherein the first data set includes activity information of the plurality of users and user attributes of the plurality of users;
determine a plurality of user segments for a behavioral change program based on the received first data set, the plurality of user segments each including a subset of the plurality of first users;
determine a second data set, the second data set being a subset of the first data set and associated with a selected user segment of the plurality of user segments;
determine a behavioral model for the selected user segment, the behavioral model comprising a statistical model of relations based on the second data set;
receive a third data set from a selected application of the plurality of applications that is associated with a selected user and a selected device, wherein the third data set includes activity information of the selected user and user attributes of the selected user;
classify the selected user into the selected user segment of the plurality of user segments based on the third data set,
determine an intervention model for the selected user based on the behavior model for the selected user segment, and,
send an intervention to the selected application according to the intervention model, wherein the intervention comprises a notification perceptible at the selected device and the intervention is sent to change behavior indicated by the activity information of the selected user.

9. The one or more computer readable storage media of claim 8, wherein the first data set includes activity information associated with a behavioral change program and the one or more computer readable storage media further include instructions to cause the one or more server computers to:
store the first data set in a data fusion module; and,
update the first data set in the data fusion module as activities of the plurality of first users take place over time to generate an updated first data set for the plurality of first users.

10. The one or more computer readable storage media of claim 9, wherein the one or more computer readable storage media further include instructions to cause the one or more server computers to:
receive the updated first data set for the plurality of first users and update the behavioral models for the selected user segment as the activities of the plurality of first users take place over time.

11. The one or more computer readable storage media of claim 9, wherein the one or more computer readable storage media further include instructions to cause the one or more server computers to determine an intervention model for the selected user by determining a conditional state of the selected user from the third data set, and mapping the conditional state to the intervention model.

12. The one or more computer readable storage media of claim 8, wherein the one or more computer readable storage media further include instructions that, when executed, cause the selected application to:
receive the interventions sent from the one or more server computers; and,
process and present the interventions to the selected user according to the intervention model.

13. A system for managing data associated with a plurality of applications on a plurality of devices operating in a communications network, the system comprising:
one or more server computers coupled to the communications network and configured to:
receive a first data set from a plurality of applications, each of the plurality of applications implemented on one of the plurality of devices and collecting data associated with one of the plurality of users for the first data set, wherein the first data set includes activity information of the plurality of users and user attributes of the plurality of users;
determine a plurality of user segments for a behavioral change program based on the received first data set, the plurality of user segments each including a subset of the plurality of first users;
determine a second data set, the second data set being a subset of the first data set and associated with a selected user segment of the plurality of user segments;
determine a behavioral model for the selected user segment, the behavioral model comprising a statistical model of relations based on the second data set;
receive a third data set from a selected application of the plurality of applications that is associated with a selected user, wherein the third data set includes first activity information of the selected user and user attributes of the selected user;
classify the selected user into the selected user segment of the plurality of user segments based on the third data set,
determine an intervention model for the selected user based on the behavior model for the selected user segment, and,
send a first intervention to the selected-application according to the intervention model, wherein the first intervention comprises a notification perceptible at a selected device of the plurality of devices on which the selected application is implemented and the intervention is sent to change behavior indicated by the first activity information of the selected user; and,
receive a fourth data set from the selected application, the fourth data set being information on a response to the first intervention sent to the selected application, the fourth data including second activity information of the selected user indicating if the first intervention changed the behavior indicated by the first activity information of the selected user.

14. The system of claim 13, wherein the system further comprises the selected-device of the plurality of devices on which the selected application is implemented, the selected device comprising:
a controller, and,
a memory including application program instructions for the selected application that when executed cause the controller to control the selected device to:
send a portion of the third data set to the system;
receive the first interventions from the one or more server computers and process the intervention.

15. The system of claim 13, wherein the one or more server computers comprise a data fusion module configured to store the first data set and update the first data set as activities of the plurality of users take place over time.

16. The system of claim 13, wherein the one or more server computers are configured to determine the intervention model for the selected user by determining a conditional state of the selected user from the third data, and, mapping the conditional state to the intervention model.

* * * * *